US012798080B2

United States Patent

(12) Tevar et al.

(10) Patent No.: US 12,798,080 B2
(45) Date of Patent: Nov. 17, 2026

(54) VARIABLY CONTROLLABLE INSTRUMENT

(71) Applicant: Plitzie LLC, Powell, OH (US)

(72) Inventors: Amul D. Tevar, Powell, OH (US); Manish Pandya, King of Prussia, PA (US); Jacob Snedeker, Encinitas, CA (US)

( * ) Notice: Subject to any disclaimer, the term of this patent is extended or adjusted under 35 U.S.C. 154(b) by 228 days.

(21) Appl. No.: 18/430,274

(22) Filed: Feb. 1, 2024

(65) Prior Publication Data

US 2024/0253204 A1 Aug. 1, 2024

Related U.S. Application Data

(60) Provisional application No. 63/482,711, filed on Feb. 1, 2023.

(51) Int. Cl.
*B25J 9/06* (2006.01)
*B25J 9/10* (2006.01)
(Continued)

(52) U.S. Cl.
CPC ............... *B25J 9/065* (2013.01); *B25J 9/104* (2013.01); *A61B 2017/00323* (2013.01);
(Continued)

(58) Field of Classification Search
CPC ... B25J 9/065; B25J 9/104; B25J 18/06; B25J 9/06; A61B 2017/00323; A61B 34/30; A61B 34/71; B25G 1/10
See application file for complete search history.

(56) References Cited

U.S. PATENT DOCUMENTS 8,069,747 B2 * 12/2011 Buckingham ............ B25J 18/06 901/15
8,608,648 B2 * 12/2013 Banik ................ A61B 1/00071 600/141
(Continued)

FOREIGN PATENT DOCUMENTS

CN 112405508 A 2/2021
CN 215149111 U 12/2021
(Continued)

OTHER PUBLICATIONS

International Search Report and Written Opinion for PCT Application No. PCT/US2024/014054, Korean Intellectual Property Office, 189 Cheongsa-ro, Seo-gu, Daejeon, 25308, Republic of Korea, May 28, 2024.

*Primary Examiner* — Jonathan M Dunlap
(74) *Attorney, Agent, or Firm* — Thomas E. Lees, LLC

(57) ABSTRACT

A variably controllable instrument is shown, which comprises multiple modified origami-type structures in series. Each modified origami-type structure interfaces with an adjacent modified origami-type structure and each modified origami-type structure has holes, which are aligned with holes from its neighboring modified origami-type structure. Cords or rivets are threaded through the aligned holes. By applying different amounts of tension in each of the cords, bends and turns are inducible at each interface between adjacent modified origami-type structures. These bends permit variable control in either transverse direction and for tools to be mounted inside, through or alongside the system. The control of the system can be manual, automated or a combination thereof.

9 Claims, 5 Drawing Sheets

(51) Int. Cl.

| | |
|---|---|
| ***B25J 18/06*** | (2006.01) |
| *A61B 17/00* | (2006.01) |
| *A61B 34/00* | (2016.01) |
| *A61B 34/30* | (2016.01) |
| *B25G 1/10* | (2006.01) |

(52) U.S. Cl.

CPC ............... *A61B 34/30* (2016.02); *A61B 34/71* (2016.02); *B25G 1/10* (2013.01); *B25J 9/06* (2013.01); *B25J 18/06* (2013.01)

(56) References Cited

U.S. PATENT DOCUMENTS

| | | | | |
|---|---|---|---|---|
| 11,278,365 | B2 * | 3/2022 | Kim | A61B 34/71 |
| 11,419,692 | B2 * | 8/2022 | Kim | A61B 34/71 |
| 11,911,014 | B2 * | 2/2024 | Kim | A61B 17/00234 |
| 12,409,571 | B1 * | 9/2025 | Graham | B25J 9/065 |
| 2005/0107667 | A1 * | 5/2005 | Danitz | A61B 34/70<br>600/139 |
| 2008/0287963 | A1 * | 11/2008 | Rogers | A61B 1/008<br>606/130 |
| 2015/0047451 | A1 | 2/2015 | Kwon | |
| 2015/0202013 | A1 * | 7/2015 | Teichtmann | A61B 17/00234<br>606/130 |
| 2018/0125596 | A1 * | 5/2018 | He | A61B 34/71 |

FOREIGN PATENT DOCUMENTS

| | | | |
|---|---|---|---|
| JP | 2019195864 | A | 11/2019 |
| KR | 101427322 | B1 | 8/2014 |

* cited by examiner

VARIABLY CONTROLLABLE INSTRUMENT

CROSS REFERENCE TO RELATED APPLICATIONS

This application claims the benefit of U.S. Provisional Patent Application Ser. No. 63/482,711, filed Feb. 1, 2023, entitled VARIABLY CONTROLLABLE INSTRUMENT, by Amul Tevar et alia, the disclosure of which is hereby incorporated herein by reference.

BACKGROUND

Field of Disclosure

Various aspects of the present invention relate generally to a controllable instrument and more specifically to a variably controllable instrument that is usable in narrow or difficult to access spaces such as aircraft, ships, vehicles, armor, walls, houses, pipeline, hatches or locations that are difficult to access or where physical access is not comfortable, etc.

Description of Related Art

Routine inspection of infrastructure and maintenance of physical assets can be difficult when assets may be under fluids, deep inside critical assets, outside of pressurized structures, buried or located behind obstructions. Therefore, there are ongoing efforts to improve systems, processes, and devices for inspecting and maintaining physical assets.

BRIEF SUMMARY

According to aspects of the present invention, a variably controllable instrument is shown, which comprises multiple modified origami-type repeating structures in series. The modified origami-type structure can interface with an adjacent modified origami-type structure or can interface with a different part of the instrument, and each modified origami-type structure may have holes, which may align with holes from its neighboring modified origami-type structure. Cords, cylinders, tubes, or other materials are threaded through the aligned holes to be used for movement, support, housing, or delivery of other tools, vacuum or transport of force or matter. By applying different or the same amount of tension in each of the cords, bends are inducible at each interface between adjacent modified origami-type structures or terminus points in the instrument. These bends permit variable control in either transverse direction and the ability for the bends to be locked or moved as needed. Other shape structures may allow for the system to maintain a close fit through different spaces or gaskets to enable moving between different environments that may be pressurized, separated, or requiring low contamination.

DETAILED DESCRIPTION

Figure 1A:
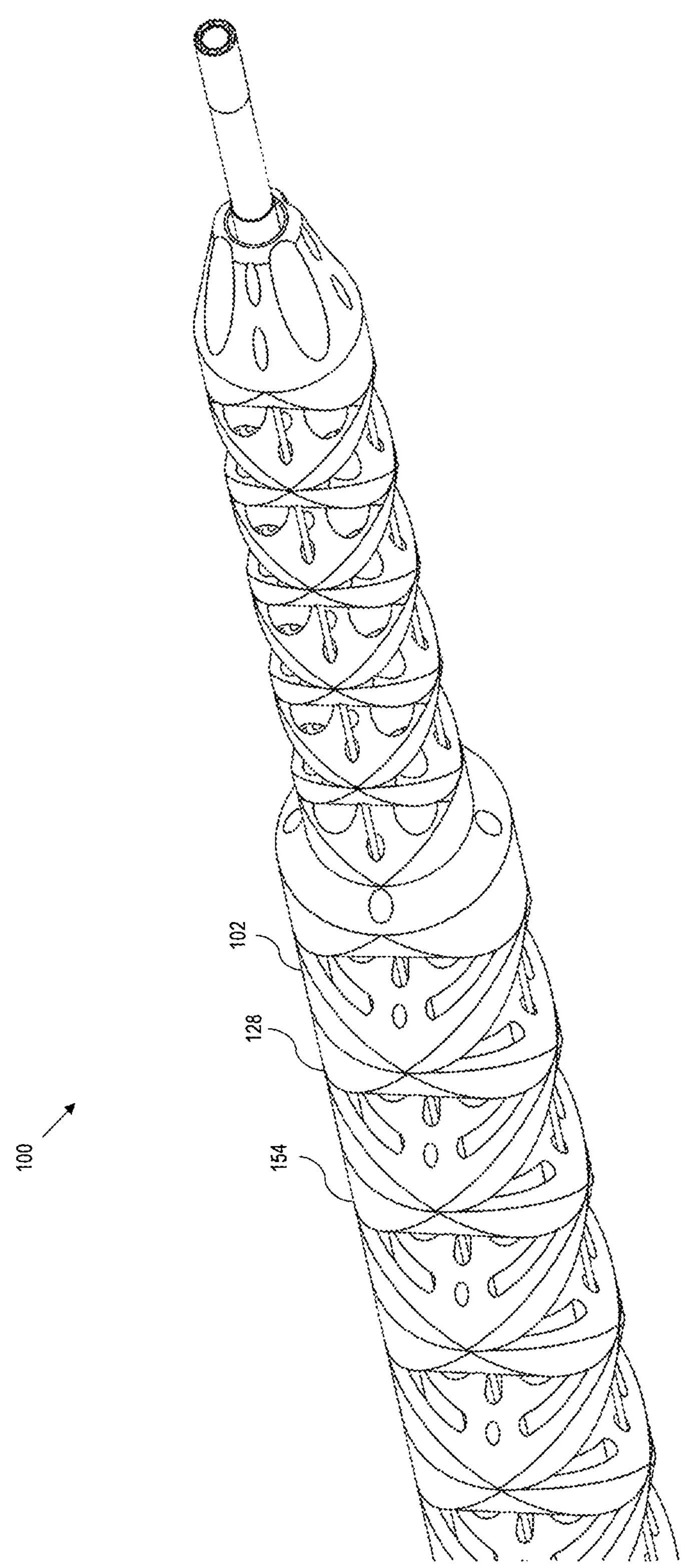
FIG. 1A a drawing that shows a perspective view of one embodiment of serially connected modified origami-type structures from an embodiment of a variably controllable instrument.

During inspection of pipes or other confined spaces, there is sometimes little room for maneuverability. Other inspections may have a large free space that has an area of interest that is difficult to examine due to placement or physical characteristics. For example, a pipe with a one-inch diameter (approximately 2.54 cm) within a ship does not leave much room for navigation of tools or cameras. When pipes have bends or confined spaces have corners, navigation becomes even more difficult. Sometimes there is a need to keep the tool or camera in different parts of an environment or application, such as looking up out of a fluid to repair an empty top part of a storage tank.

To address the difficulties associated with maneuvering within confined spaces, this disclosure teaches a variably controllable instrument with multiple modified origami-type structures that are connected in series. Each modified origami-type structure can interface with an adjacent modified origami-type structure and each modified origami-type structure may have similar or different holes, which may align with holes from its neighboring modified origami-type structure or be adjacent to other structures of the tool. Cords, tubes, cylinders, wiring, tools, rivets, or other materials are threaded through the aligned holes. Tools, sensors, implements, actuators can be mounted inside, through or alongside the system. Additional branch origami-type structures may be added to enable multiple independent systems sharing an origin point. By applying different amounts of tension in each of the cords or other materials placed between the origami-type structures, bends are inducible at each interface between adjacent modified origami-type structures. These bends permit variable control in either transverse direction. The same holes may be made larger, smaller, or different to also be aligned to allow the addition or insertion of other tools or transport of material inside or along the tool. The tension may be applied manually, through machines or actuators, or a combination of both. By varying the geometries or lack thereof of the structures, different stiffnesses, support structures, or movements can be enabled.

With this broad description of the technical solution for the technical problem in mind, attention is now turned to FIGS. 1A through 4, which show specific embodiments of variably controllable instruments with modified origami-type structures that enable movement of the origami-type structures, insertion and mounting of other tools or features inside or on the tool, and a variety of shapes, alignments, terminus points, and configurations to enable faster, safer access to locations. Functionally, each modified origami-type structure contacts its adjacent modified origami-type structure to allow angular, fixed, or pivotal movement at the contact point. Because the modified origami-type structure has a major axis on one end that is skew with the major axis on the other end, the permissible angular movement alternates at every other contact (e.g., left-right bend at every odd contact point, up-down bend at every even contact point, etc.). This permits all of the angular possibilities that are provided by multiple serially connected universal joints, but with fewer components. Different origami shapes may be mixed or used to enable different characteristics for movement and tool insertion. Furthermore, threading multiple cords through the modified origami-type structures in the axial direction permits various degrees of angular control for the length of the apparatus. In other words, each pair of adjacent modified origami-type structures behaves similarly to how a joints and muscles work and may have variations to enable different behaviors or functionalities. Tension, fixtures, attachment points, and tools can be placed at symmetrical or non-linear points of a tool to enable use case customization.

Figure 1B:
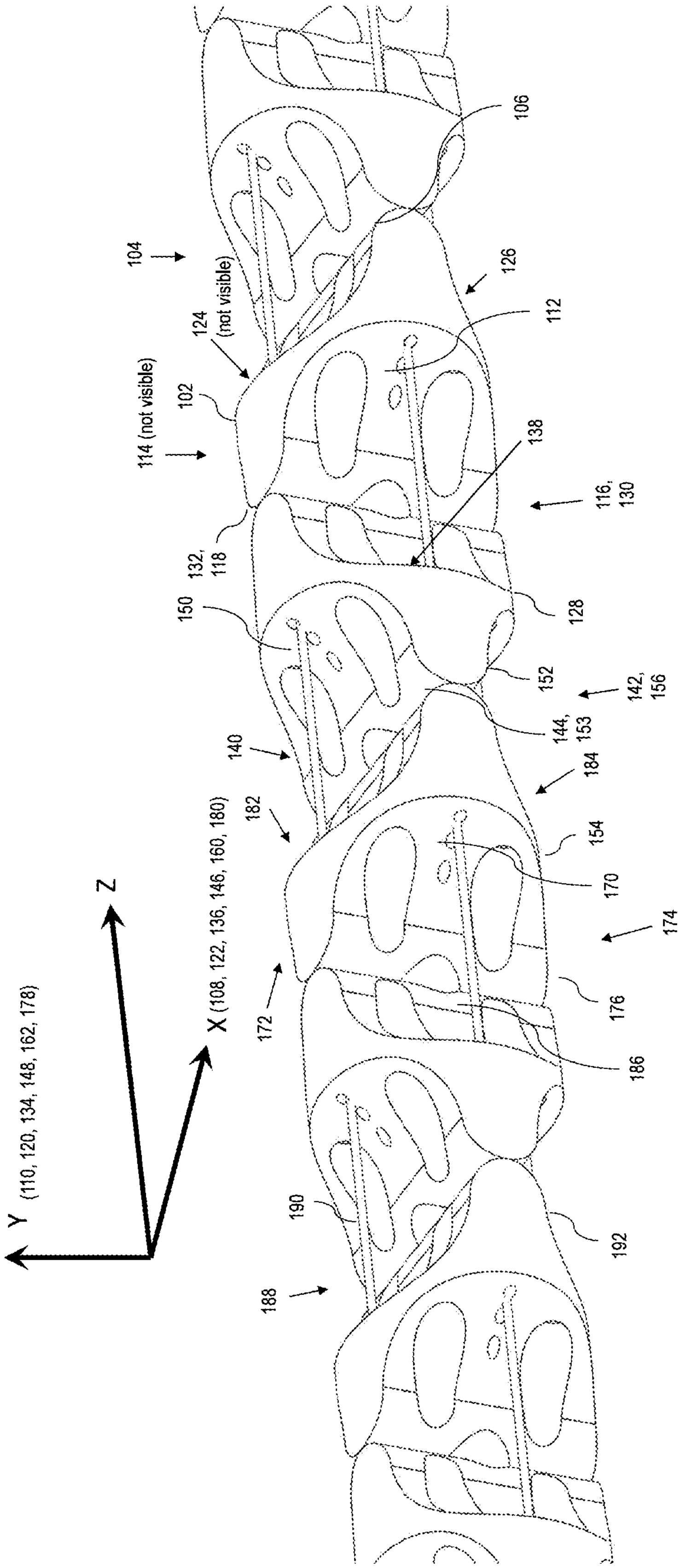
FIG. 1B is drawing that shows an enlarged view of a portion of the serially connected modified origami-type structures from FIG. 1A.

With this in mind, for context, FIGS. 1A and 1B (collectively, FIG. 1) show three-dimensional (3D) perpendicular axes of X (first transverse direction), Y (second transverse direction), and Z (axial direction) to clearly illustrate structures as well as orientations of structural components. For clarity, structural relationships between components are described first and, thereafter, functional aspects are discussed. Moreover, because details are more clearly visible in FIG. 1B, reference numerals are shown completely in FIG. 1B, while only a subset of the reference numerals are shown in FIG. 1A.

With this in mind, as shown in FIG. 1, one embodiment of the invention comprises an apparatus 100, which is aligned axially along Z with its two (2) transverse axes aligned along X and Y. The apparatus 100 comprises a modified origami-type structure 102, specifically designated as a first modified origami-type structure 102 (as there will be more later). The first modified origami-type structure 102 has a first anterior end 104 that is located at a first axial location (e.g., +Z). The first anterior end 104 comprises a substantially flat first anterior surface 106, which is shown to have a first anterior major axis 108 (e.g., along X) and a first anterior minor axis 110 (e.g., along Y). At one location (e.g., +X) on the first anterior surface 106, the modified origami-type structure 102 has a first hole 112, which extends axially (e.g., in the Z-direction) through the first modified origami-type structure 102. At an approximately symmetrically opposite location (e.g., −X), the first anterior surface 104 has a second hole 114 (not visible), which also extends axially (e.g., in the Z-direction) through the first modified origami-type structure 102.

At a second axial location (e.g., −Z) on an opposite axial end of the first modified origami-type structure is a first posterior end 116. The first posterior end 116 comprises a substantially flat first posterior surface 118. Although the substantially flat first posterior surface 118 has a first posterior major axis 120 and a first posterior minor axis 122, these axes are skew with their respective counterparts on the anterior end (meaning, e.g., the first posterior major axis 120 extends in the Y-direction, while the first posterior minor axis 122 extends in the X-direction). There is a third hole 124 (not visible) at a location on the first posterior surface along the first posterior major axis 120 (e.g., at +Y), with the third hole 124 extending axially through the first modified origami-type structure 102. Similarly, a fourth hole 126 (not visible) is located at an approximately symmetrically opposite location (e.g., −Y) on the first posterior surface 118, with the fourth hole 126 extending axially through the first modified origami-type structure 102. This modified origami-type structure 102 is a primary building block that repeats serially to form a variably controllable instrument.

Continuing, the apparatus 100 comprises a second modified origami-type structure 128 that, in appearance and structure, looks substantially similar to the first modified origami-type structure 102. As such, the second modified origami-type structure 128 comprises a second anterior end 130. The second anterior end 130 is collocated with the first posterior end 116 (e.g., at the second axial location). This is because the second anterior end 130 is adapted to contact the first posterior end 116, thereby permitting angular arrangement between the two origami-type structures 102, 128. As such, the second anterior end 130 comprises a substantially flat second anterior surface 132, which is adapted to contact the first posterior surface 118 in such a way that the second anterior surface 132 is in alignment with the first posterior surface 118. In other words, the second anterior surface 132 comprises a second anterior major axis 134 that is substantially parallel to the first posterior major axis 120 (meaning, e.g., both of the major axes 120, 130 extend in the Y-direction). The second anterior end surface 132 also has a second anterior minor axis 136, which runs in parallel to the first posterior minor axis 122 (meaning, e.g., along the X-direction). A fifth hole 138 (not visible) is at on the second anterior surface 132 (e.g., at +Y), with the fifth hole 138 extending axially through the second modified origami-type structure 128. A sixth hole 140 (not visible) also exists (at e.g., a location −Y on the second anterior surface 132), also extending axially through the second modified origami-type structure 128.

Similar to the first origami-type structure 102, the second origami-type structure 128 comprises a posterior end 142 (designated as a second posterior end 142), which is located at a third axial location. The second posterior end 142 comprises a substantially flat second posterior surface 144, which has a second posterior major axis 146 (e.g., along X) and a second posterior minor axis 148 (e.g., along Y). A seventh hole 150 is located on the first posterior surface 144 (e.g., at a location +X), along with an eighth hole 152 (e.g., at a location −X). Both the seventh hole 150 and the eighth hole 152 extend axially through the second modified origami-type structure 128.

The apparatus 100 further comprises a third modified origami-type structure 154. As shown in FIG. 1, the third modified origami-type structure 154 is substantially similar in size and function to both the first modified origami-type structure 102 and the second modified origami-type structure 128. The structural orientation between the second modified origami-type structure 128 and the third modified origami-type structure 154 is skew to the structural orientation between the first modified origami-type structure 102 and the second modified origami-type structure 128. With this skew orientation, the first two (2) origami-type structures 102, 128 allow for pivoting or bending in one direction (e.g., left-and-right), while the second two (2) origami-type structures 128, 154 allow for pivoting or bending in another (nearly perpendicular) direction (e.g., up-and-down). For brevity, the structures of the third modified origami-type structure 154 are listed without a detailed explanation of their respective orientations or functions because those orientations and functions are described above, with reference to the first and second modified origami-type structures 102, 128. Thus, one having ordinary skill in the art will be able to determine the orientation and function from the above-recited description.

With that in mind, the third modified origami-type structure 154 comprises a third anterior end 156, a substantially flat third anterior surface 158, a third anterior major axis 160 (e.g., along X), a third anterior minor axis 162 (e.g., along Y), a ninth hole 170, a tenth hole 172 (not visible), a third posterior end 174, a substantially flat third posterior surface 176, a third posterior major axis 178 (e.g., along Y), a third posterior minor axis 180 (e.g., along X), a eleventh hole 182, and a twelfth hole 184, all of which serve substantially the same function as their respective counterparts in the first and second modified origami-type structures 102, 128.

Next, the apparatus 100 further comprises a first cord 186, a second cord 188, a third cord 190, and a fourth cord 192. The first cord 186 is threaded through the first hole 112, the fifth hole 138, and the ninth hole 170, thereby linking together the modified origami-type structures 102, 128, 154 on one side. The second cord 188 is threaded through the second hole 114, the sixth hole 140, and the tenth hole 172, thereby linking together the modified origami-type structures 102, 128, 154 on an axially opposite side as the first cord 186. Next, the third cord 190 is threaded through the third hole 124, the seventh hole 150, and the eleventh hole 182 (not visible), thereby linking together the modified origami-type structures 102, 128, 154 at a location that is substantially transversely perpendicular to the location of the first and second cords 186, 188. On the axially opposite side of the third cord 190, the fourth cord 192 is threaded through the fourth hole 126, the eighth hole 152, and the twelfth hole 184 (not visible). Each of these cords 186, 188, 190, 192, when pulled, applies tension along one axial side of the apparatus 100, thereby resulting in the apparatus 100 curling in the direction of the cord that is pulled. This allows the apparatus 100 to bend up, down, left, right, or in any other transverse direction (X or Y) in relation to the axial direction (Z). In other words, in relation to the Z-axis, the apparatus 100 is bendable at any azimuthal angle.

For clarity, in operation, when force or tension is applied to the first cord 186, the apparatus 100 bends in one angular transverse direction (e.g., left). When force or tension is applied to the third cord 190, the apparatus 100 bends in an opposite angular transverse direction (e.g., right). Similarly, when force or tension is applied to the second cord 188 or the fourth cord 192, the apparatus 100 bends in yet other angular transverse directions (e.g., up or down, respectively). As one can appreciate, force or tension applied to different combinations of cords 186, 188, 190, 192 will permit the apparatus 100 to bend in many different ways. For some embodiments, the apparatus 100 can curl into a ball (similar to how a head of a fern curls).

Other origami-type shapes or spacing will enable different parts of the system to be moved in any direction (X, Y, Z) similar to a finger that is able to be bent, extended, hyper-extended, rotated or a combination of movements to enable biological type or machine type movement. In other words, the tools can be manipulated like a gimbal without having a gimbal.

As one having skill in the art will appreciate, although only three (3) modified origami-type structures 102, 128, 154 have been described in detail, FIG. 1 shows that more origami-type structures can be serially coupled to create a longer apparatus, which has a longer reach. With enough modified origami-type structures serially coupled, one can increase both the reach and the angular variation in the apparatus 100.

Figure 2:
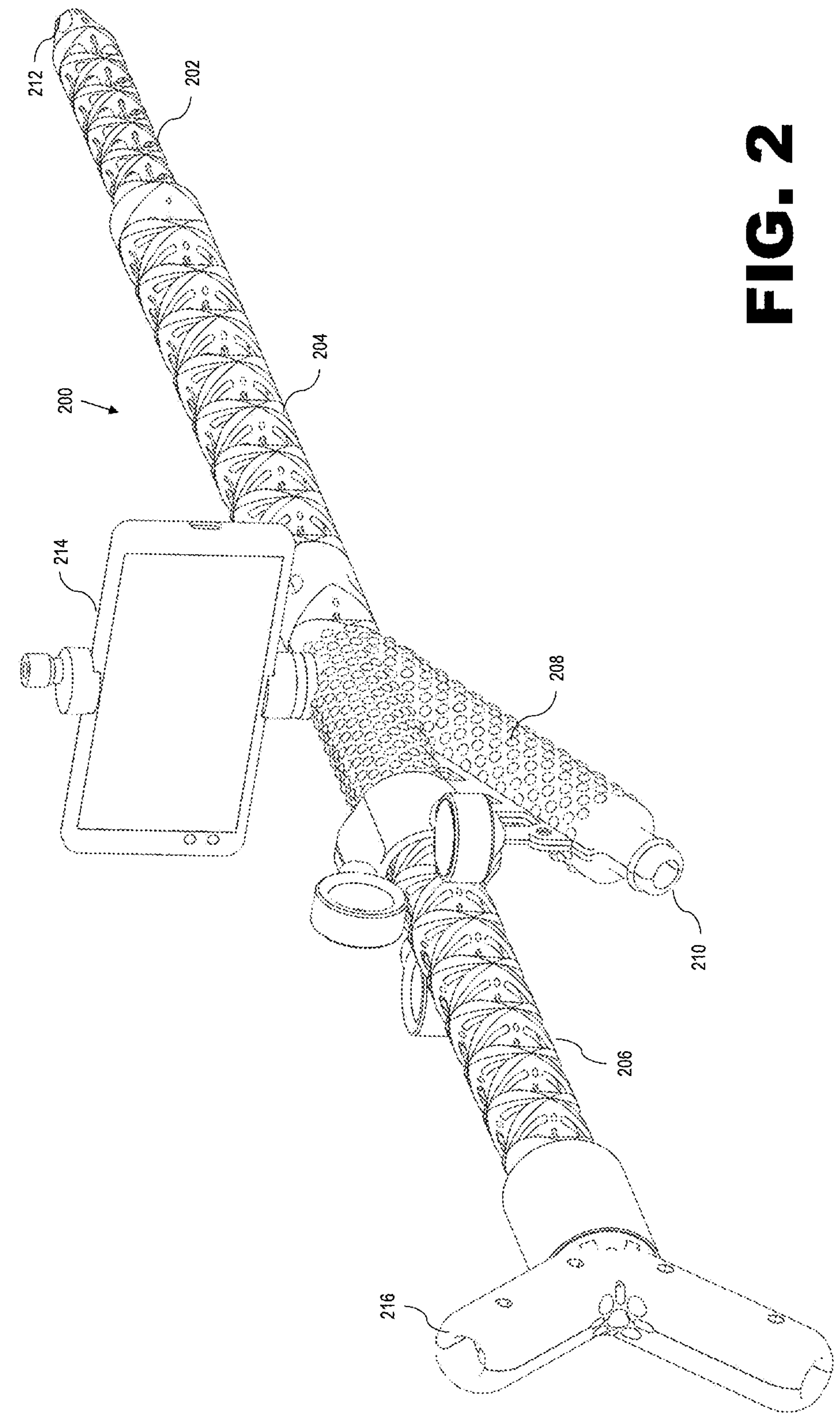
FIG. 2 is drawing that shows a perspective view of one embodiment of a variably controllable instrument comprising the modified origami-type structures of FIGS. 1A and 1B (collectively, "FIG. 1").

Turning now to FIG. 2, shown is a perspective view of one embodiment of a variably controllable instrument 200 comprising the apparatus 100 of FIG. 1. As shown in FIG. 2, the instrument 200 comprises a first segment 202 (front), second segment 204 (middle) in series with the first segment 202, and a third segment 206 (back) in series with the second segment 204. The first segment 202 comprises the apparatus 100 with smaller diameter modified origami-type structures, while the second segment 204 comprises the apparatus 100 with larger diameter modified origami-type structures, thereby demonstrating an ability to accommodate inspection of different size pipes or spaces.

Between the second segment 204 and the third segment 206, the instrument 200 comprises a branch point 208 with an orifice 210 through which the cords 186, 188, 190, 192 pass, thereby allowing for control of the first and second segments 202, 204 by manipulation of the cords (not shown). For some embodiments, a miniature camera 212 is mounted at the front end of the first segment 202 and a display screen 214 is attached to the instrument 200 at the branch point 208 to show what the camera 212 captures as it progresses through a pipe. Some embodiments also include a handle 216, which can serve as yet another branch point, should the third segment 206 include the variably controllable apparatus 100 of FIG. 1.

Figure 3:
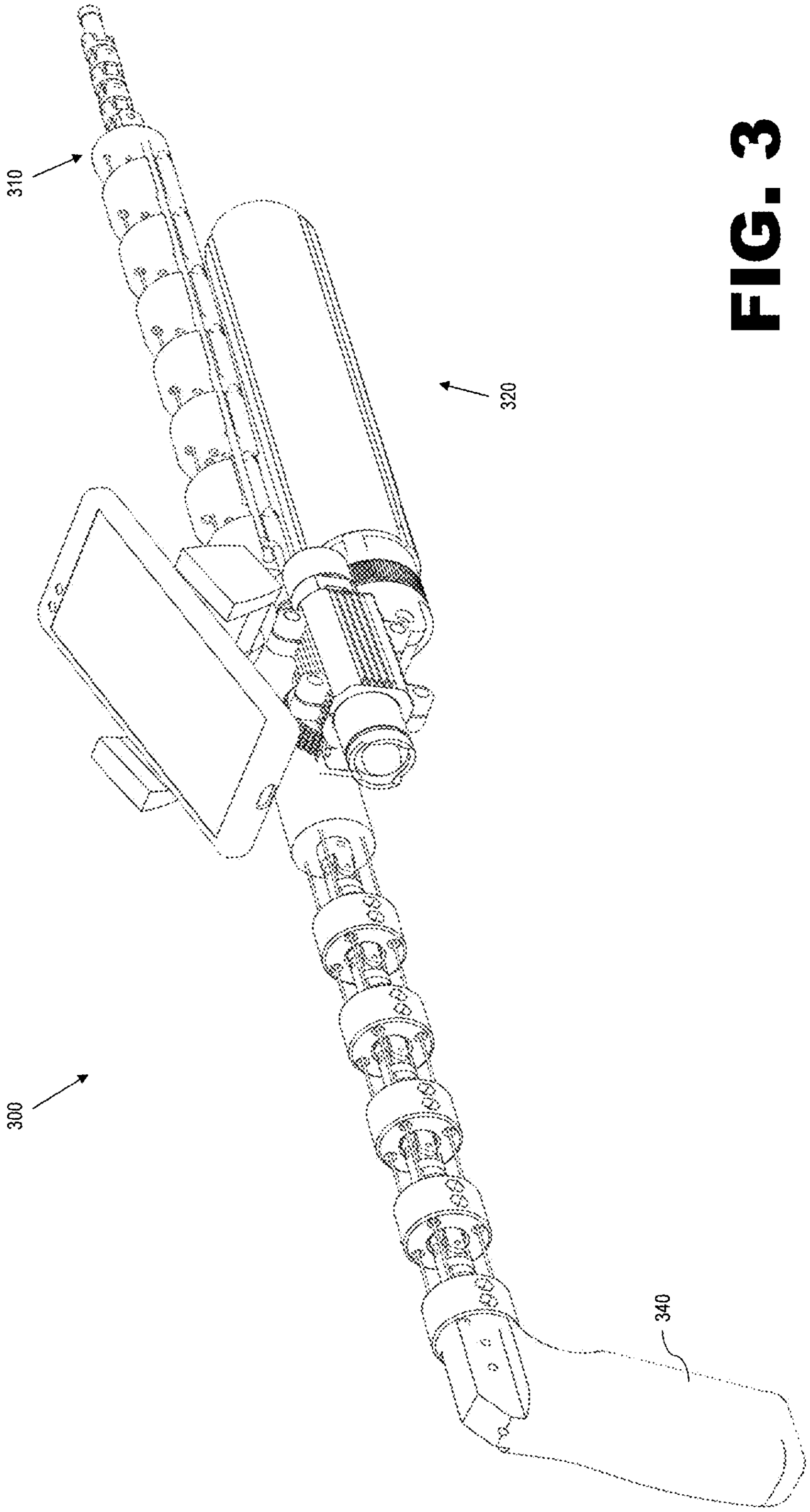
FIG. 3 is a drawing that shows a perspective view of another embodiment of a variably controllable instrument comprising the modified origami-type structures of FIG. 1.
Figure 4:
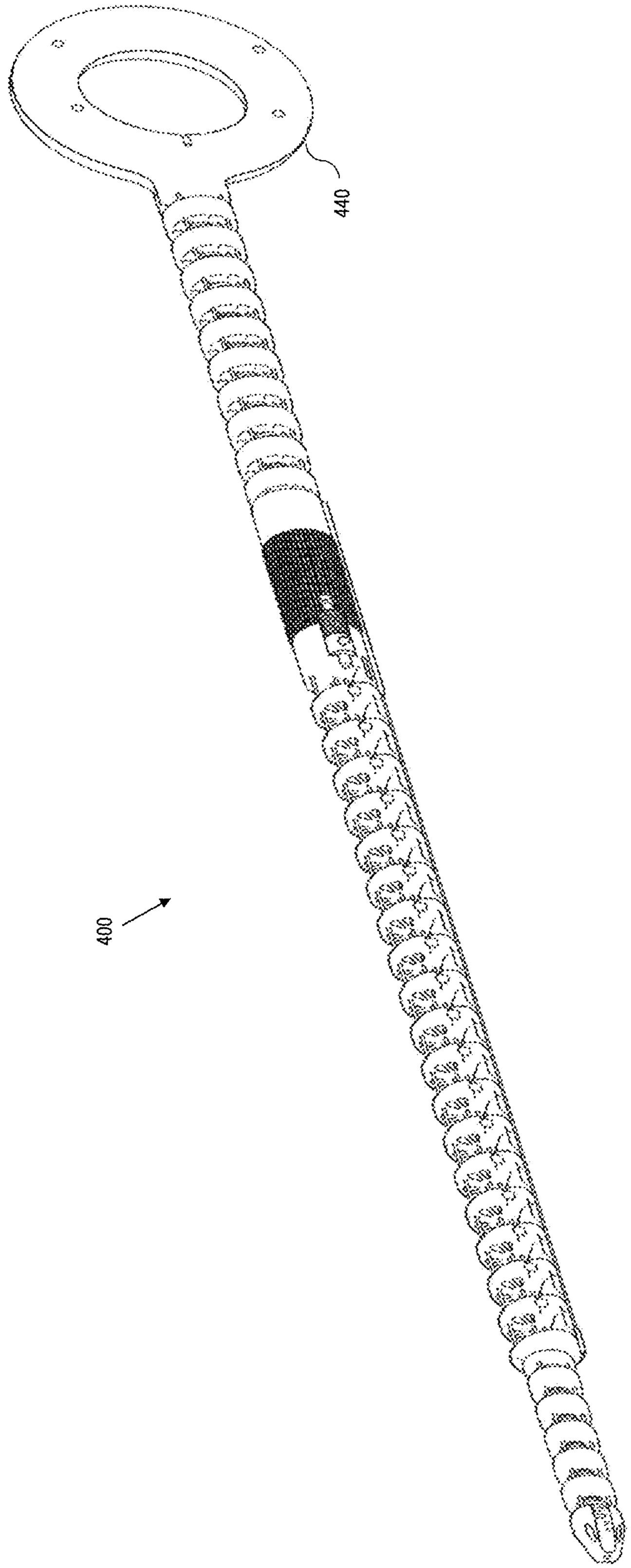
FIG. 4 is a perspective view showing yet another embodiment of a a variably controllable instrument comprising the modified origami-type structures of FIG. 1.

FIGS. 3 and 4 show a perspective views of yet other embodiments of variably controllable instruments 300, 400 comprising the apparatus 100 of FIG. 1. As one can see, the structures and functions of FIGS. 3 and 4 are similar to the structures and functions of FIG. 2. However, both FIGS. 3 and 4 demonstrate how different addons 310, 320 (e.g., sensors, cameras, etc.) are mountable on the instruments 300, 400 as may be needed or desired. Similarly, FIGS. 3 and 4 demonstrate how the instruments 300, 400 accommodate different handles 340, 440, which may be suitable for different purposes. Because those having ordinary skill in the art will understand the interchangeability of handles 340, 440 and addons 310, 320, further discussions of handles and addons are omitted herein.

As shown in FIGS. 1 through 4, by providing a variably controllable apparatus 100 with repeating modified origami-type structures 102, 128, 154, the inspection instruments 200, 300, 400, which are shown and described above, have greater flexibility and possibly greater reach, thereby permitting better inspection and diagnoses of confined spaces.

For example, other embodiments may include an apparatus that has a spring-interposed structure. An example of such an embodiment comprises a first structure, which comprises a substantially flat first anterior surface. The first anterior structure comprises a first hole at a first location on the first anterior surface, the first hole extending axially through the first structure, a second hole at a second location on the first anterior surface, the second hole extending axially through the first structure, a third hole at a third location on the first anterior surface, the third hole extending axially through the first structure; and a fourth hole at fourth location on the first anterior surface, the fourth hole extending axially through the first structure. The first structure further comprises a substantially flat first posterior surface. The apparatus further comprises a first spring with a first spring anterior end connected to the first posterior surface. The first spring also has a first spring posterior end. The apparatus also comprises a second structure with a substantially flat second anterior surface connected to the first spring posterior end. The second anterior surface comprises a fifth hole at a fifth location on the second anterior surface, the fifth hole extending axially through the second structure, a sixth hole at a sixth location on the second anterior surface, the sixth hole extending axially through the second structure, a seventh hole at a seventh location on the second anterior surface, the seventh hole extending axially through the second structure, and an eighth hole at an eighth location on the second anterior surface, the eighth hole extending axially through the second structure. The second structure also comprises a substantially flat second posterior surface. The apparatus also includes a second spring with a second spring anterior end connected to the second posterior surface. The second spring also has a second spring posterior end. The apparatus further comprises a third structure. The third structure comprises a substantially flat third anterior surface connected to the second spring posterior end. The third anterior surface comprises a ninth hole at a fifth location on the third anterior surface, the ninth hole extending axially through the third structure, a tenth hole at a sixth location on the third anterior surface, the tenth hole extending axially through the third structure, an eleventh hole at a seventh location on the third anterior surface, the eleventh hole extending axially through the third structure, and a twelfth hole at an eighth location on the third anterior surface, the twelfth hole extending axially through the third structure. The third structure also comprises a substantially flat third posterior surface. The apparatus also includes a first cord threaded through the first hole, the first cord further being threaded through the fifth hole, the first cord further being threaded through the ninth hole. The apparatus further comprises a second cord threaded through the second hole, the first cord further being threaded through the sixth hole, the first cord further being threaded through the tenth hole. The apparatus further comprises a third cord threaded through the third hole, the first cord further being threaded through the seventh hole, the first cord further being threaded through the eleventh hole. The apparatus further comprises a fourth cord threaded through the fourth hole, the first cord further being threaded through the eighth hole, the first cord further being threaded through the twelfth hole.

Yet other embodiments may include an apparatus that has a structure that substantially mimics a vertebra. Such an apparatus extends axially along a predefined axis and comprises a first structure, a second structure, a third structure, a first spring, a second spring, and a cord. The first structure comprises a first structure anterior end with a first hole at a first location on the first structure anterior end. The first hole extends axially through the first structure. The first structure also has a first structure posterior end. The first spring comprises a first spring anterior end connected to the first structure posterior end. The first spring also has a first spring posterior end. The second structure comprises a second structure anterior end connected to the first spring posterior end, with the second structure anterior end comprising a second hole at a second location on the second structure anterior end, with the second hole extending axially through the second structure. The second structure also includes a second structure posterior end. The second spring has a second spring anterior end connected to the second structure posterior surface. The second spring further comprises a second spring posterior end. The third structure comprises a third structure anterior end connected to the second spring posterior end, with the third structure anterior surface comprising a third hole at a third location on the third structure anterior end, with the third hole extending axially through the third structure. The cord is threaded through the first hole, the second hole, and the third hole.

The terminology used herein is for the purpose of describing particular embodiments only and is not intended to be limiting of the invention. As used herein, the singular forms “a”, “an” and “the” are intended to include the plural forms as well, unless the context clearly indicates otherwise. It will be further understood that the terms “comprises” and/or “comprising,” when used in this specification, specify the presence of stated features, integers, steps, operations, elements, and/or components, but do not preclude the presence or addition of one or more other features, integers, steps, operations, elements, components, compounds, transportable objects, data types and/or groups thereof.

Furthermore, Applicant expressly defines the term “modified origami-type structure” to mean any unit with substantially interconnectable ends that enables at least one state of movement between linear to curved states of the tool, with the internal modified origami-type structure allowing some method of connection to another unit or a part of the tool and possibly able to house connectors or space for other features needed by the user. At least two repeated origami-type structures would be used in sequence in the tool with at least two terminus points to other parts of the tool, and different or similar modified origami-type structures with tool structures could be used to create movement. By way of example, and not by way of limitation due to shape, curvature, surface texturing, internal structure, modified origami-type structures are expressly defined to include sphericons with flat ends and all Johnson solids that exhibit a gyro-bi configuration (which is shown in https://en.wikipedia.org/wiki/Johnson_solid (e.g., gyrobicupola, gyrobiprism, etc.), or origami-type structures that are mixture of non-linear and linear structures similar to biologically or generative designed support structures that may not follow defined models but will have at least one (1) geometrically definable surface or location for attachment to other structures.

The corresponding structures, materials, acts, and equivalents of all means or step plus function elements in the claims below are intended to include any structure, material, or act for performing the function in combination with other claimed elements as specifically claimed. The description of the present disclosure has been presented for purposes of illustration and description, but is not intended to be exhaustive or limited to the invention in the form disclosed. Many modifications and variations will be apparent to those of ordinary skill in the art without departing from the scope and spirit of the invention. Aspects of the disclosure were chosen and described in order to best explain the principles of the invention and the practical application, and to enable others of ordinary skill in the art to understand the invention for various embodiments with various modifications as are suited to the particular use contemplated.

What is claimed is:

1. An apparatus, comprising:

a first axis extending axially along an axial direction (Z);

a second axis extending transversely along a first transverse direction (X), X being substantially perpendicular to Z;

a third axis extending transversely along a second transverse direction (Y), Y being substantially perpendicular to X, Y further being substantially perpendicular to Z;

a first modified origami-type structure comprising:

a first anterior end at a first axial location (+Z), the first anterior end comprising:

a substantially flat first anterior surface comprising:

a first anterior major axis along X; and a first anterior minor axis along Y;

a first hole at a location +X on the first anterior surface, the first hole extending axially through the first modified origami-type structure; and a second hole at a location −X on the first anterior surface, the second hole extending axially through the first modified origami-type structure; and a first posterior end at a second axial location (−Z), the first posterior end comprising:

a substantially flat first posterior surface comprising:

a first posterior major axis along Y; and a first posterior minor axis along X;

a third hole at a location +Y on the first posterior surface, the third hole extending axially through the first modified origami-type structure; and a fourth hole at location −Y on the first posterior surface, the fourth hole extending axially through the first modified origami-type structure;

a second modified origami-type structure comprising:

a second anterior end at the second axial location, the second anterior end adapted to contact the first posterior end, the second anterior end comprising:

a substantially flat second anterior surface adapted to contact the first posterior surface, the second anterior surface being in alignment with the first posterior surface, the second anterior surface comprising:

a second anterior major axis along Y; and a second anterior minor axis along X;

a fifth hole at a location +Y on the second anterior surface, the fifth hole extending axially through the second modified origami-type structure; and a sixth hole at a location −Y on the second anterior surface, the sixth hole extending axially through the second modified origami-type structure; and a second posterior end located at a third axial location, the second posterior end comprising:

a substantially flat second posterior surface comprising:

a second posterior major axis along X; and a second posterior minor axis along Y;

a seventh hole at a location +X on the first posterior surface, the seventh hole extending axially through the second modified origami-type structure; and an eighth hole at location −X on the first posterior surface, the eighth hole extending axially through the second modified origami-type structure;

a third modified origami-type structure comprising:

a third anterior end at the third axial location, the third anterior end adapted to contact the second posterior end, the third anterior end comprising:

a substantially flat third anterior surface adapted to contact the second posterior surface, the third anterior surface being in alignment with the second posterior surface, the third anterior surface comprising:

a third anterior major axis along X; and a third anterior minor axis along Y;

a ninth hole at a location +X on the third anterior surface, the ninth hole extending axially through the third modified origami-type structure; and a tenth hole at a location −X on the third anterior surface, the tenth hole extending axially through the third modified origami-type structure; and a third posterior end located at a fourth axial location, the third posterior end comprising:

a substantially flat third posterior surface comprising:

a third posterior major axis along Y; and a third posterior minor axis along X;

an eleventh hole at a location +Y on the third posterior surface, the eleventh hole extending axially through the third modified origami-type structure; and a twelfth hole at location −Y on the third posterior surface, the twelfth hole extending axially through the third modified origami-type structure;

a first cord threaded through the first hole, the first cord further being threaded through the fifth hole, the first cord further being threaded through the ninth hole;

a second cord threaded through the second hole, the first cord further being threaded through the sixth hole, the first cord further being threaded through the tenth hole;

a third cord threaded through the third hole, the first cord further being threaded through the seventh hole, the first cord further being threaded through the eleventh hole; and a fourth cord threaded through the fourth hole, the first cord further being threaded through the eighth hole, the first cord further being threaded through the twelfth hole;

a flexible front segment axially centered along Z and comprising a first diameter;

a flexible middle segment axially centered along Z and positioned in series with the flexible front segment, the flexible middle segment comprising a second diameter, the second diameter being larger than the first diameter;

a flexible back segment axially centered along Z and positioned in series with the flexible middle segment, the flexible back segment comprising:

the first modified origami-type structure;

the second modified origami-type structure; and the third modified origami-type structure; and a display screen located between the flexible middle segment and the flexible back segment.

2. The apparatus of claim 1, wherein the cord comprises twine, wire, tube, or flexible cylinder.

3. The apparatus of claim 1 wherein the first modified origami-type structure comprises at least one selected from the group consisting of: oloid, sphericon, gyrobicupola, gyrobiprism, a Johnson solid that exhibits a gyro-bi configuration, or any other convex or concave solid that exhibits a gyro-bi configuration.

4. An apparatus, comprising:

a first structure comprising:

a substantially flat first anterior surface comprising:

a first hole at a first location on the first anterior surface, the first hole extending axially through the first structure;

a second hole at a second location on the first anterior surface, the second hole extending axially through the first structure;

a third hole at a third location on the first anterior surface, the third hole extending axially through the first structure; and a fourth hole at fourth location on the first anterior surface, the fourth hole extending axially through the first structure; and a substantially flat first posterior surface;

a second structure comprising:

a substantially flat second anterior surface connected to the substantially flat first posterior surface, the second anterior surface comprising:

a fifth hole at a fifth location on the second anterior surface, the fifth hole extending axially through the second structure;

a sixth hole at a sixth location on the second anterior surface, the sixth hole extending axially through the second structure;

a seventh hole at a seventh location on the second anterior surface, the seventh hole extending axially through the second structure; and an eighth hole at an eighth location on the second anterior surface, the eighth hole extending axially through the second structure; and a substantially flat second posterior surface;

a third structure comprising:

a substantially flat third anterior surface connected to the substantially flat second posterior surface, the third anterior surface comprising:

a ninth hole at a fifth location on the third anterior surface, the ninth hole extending axially through the third structure;

a tenth hole at a sixth location on the third anterior surface, the tenth hole extending axially through the third structure;

an eleventh hole at a seventh location on the third anterior surface, the eleventh hole extending axially through the third structure; and a twelfth hole at an eighth location on the third anterior surface, the twelfth hole extending axially through the third structure; and a substantially flat third posterior surface;

a first cord threaded through the first hole, the first cord further being threaded through the fifth hole, the first cord further being threaded through the ninth hole;

a second cord threaded through the second hole, the first cord further being threaded through the sixth hole, the first cord further being threaded through the tenth hole;

a third cord threaded through the third hole, the first cord further being threaded through the seventh hole, the first cord further being threaded through the eleventh hole; and a fourth cord threaded through the fourth hole, the first cord further being threaded through the eighth hole, the first cord further being threaded through the twelfth hole;

a flexible front segment comprising:

a first axial center; and a first diameter;

a flexible middle segment positioned in series with the flexible front segment, the flexible middle segment comprising:

a second axial center aligned with the first axial center; and a second diameter larger than the first diameter;

a flexible back segment positioned in series with the flexible middle segment, the flexible back segment comprising:

a third axial center aligned with the second axial center;

the first modified origami-type structure;

the second modified origami-type structure; and the third modified origami-type structure; and a display screen located between the flexible middle segment and the flexible back segment.

5. The apparatus of claim 4, wherein the cord comprises twine, wire, tube, or flexible cylinder.

6. The apparatus of claim 4, wherein the first structure comprises at least one selected from the group consisting of: oloid, sphericon, gyrobicupola, gyrobiprism, a Johnson solid that exhibits a gyro-bi configuration, or any other convex or concave solid that exhibits a gyro-bi configuration.

7. An apparatus extending axially along a predefined axis, comprising:

a first structure comprising:

a first structure anterior end comprising:

a first hole at a first location on the first structure anterior end, the first hole extending axially through the first structure; and a first structure posterior end;

a second structure pivotally connected to the first structure, the second structure comprising:

a second structure anterior end connected to the first structure posterior end, the second structure anterior end comprising:

a second hole at a second location on the second structure anterior end, the second hole extending axially through the second structure;

a second structure posterior end;

a third structure comprising:

a third structure anterior end connected to the second structure posterior surface, the third structure anterior surface comprising:

a third hole at a third location on the third structure anterior end, the third hole extending axially through the third structure;

a cord threaded through the first hole, the first cord further being threaded through the second hole, the first cord further being threaded through the third hole;

a flexible front segment comprising:

a first axial center; and a first diameter;

a flexible middle segment positioned in series with the flexible front segment, the flexible middle segment comprising:

a second axial center aligned with the first axial center; and a second diameter larger than the first diameter;

a flexible back segment positioned in series with the flexible middle segment, the flexible back segment comprising:

a third axial center aligned with the second axial center;

the first structure;

the second structure; and the third structure; and a display screen located between the flexible middle segment and the flexible back segment.

8. The apparatus of claim 7, wherein the cord comprises twine, wire, tube, or flexible cylinder.

9. The apparatus of claim 7 wherein the first structure comprises at least one selected from the group consisting of: oloid, sphericon, gyrobicupola, gyrobiprism, a Johnson solid that exhibits a gyro-bi configuration, or any other convex or concave solid that exhibits a gyro-bi configuration.

* * * * *